United States Patent [19]
Balbierz

[11] Patent Number: 5,902,282
[45] Date of Patent: May 11, 1999

[54] STEP-DOWN CATHETER

[75] Inventor: Daniel J. Balbierz, Redwood City, Calif.

[73] Assignee: Johnson & Johnson Medical, Inc., Arlington, Tex.

[21] Appl. No.: 08/774,975

[22] Filed: Dec. 26, 1996

[51] Int. Cl.[6] .................................................. A61M 5/00
[52] U.S. Cl. ........................... 604/264; 604/53; 604/158; 604/164; 604/280
[58] Field of Search ................. 604/49, 51–53, 604/96, 104, 158, 160, 161, 164, 166, 171, 264, 280

[56] References Cited

U.S. PATENT DOCUMENTS

| | | | |
|---|---|---|---|
| 3,677,243 | 7/1972 | Nerz | 604/161 |
| 3,877,429 | 4/1975 | Rasumoff | 604/158 |
| 4,471,778 | 9/1984 | Toye | 604/160 |
| 4,596,559 | 6/1986 | Fleischhacker | 604/161 |
| 4,710,181 | 12/1987 | Fuqua . | |
| 4,716,901 | 1/1988 | Jackson et al. | 604/160 |
| 4,921,479 | 5/1990 | Grayzel | 604/160 |
| 4,976,703 | 12/1990 | Franetzki et al. | 604/280 |
| 4,983,168 | 1/1991 | Moorehead | 604/161 |
| 5,073,166 | 12/1991 | Parks et al. . | |
| 5,158,545 | 10/1992 | Trudell et al. | 604/104 |
| 5,167,634 | 12/1992 | Corrigan, Jr. et al. | 604/161 |
| 5,183,464 | 2/1993 | Dubrul et al. . | |
| 5,318,588 | 6/1994 | Horzewski et al. | 604/104 |
| 5,380,307 | 1/1995 | Rhee et al. . | |
| 5,407,430 | 4/1995 | Peters . | |
| 5,431,676 | 7/1995 | Dubrul et al. . | |
| 5,454,790 | 10/1995 | Dubrul | 604/104 |
| 5,474,537 | 12/1995 | Solar . | |
| 5,496,275 | 3/1996 | Sirhan et al. . | |
| 5,569,197 | 10/1996 | Helmus et al. | 604/53 |

FOREIGN PATENT DOCUMENTS

| | | |
|---|---|---|
| 0453234A | 4/1991 | European Pat. Off. . |
| 3107983A | 3/1981 | Germany . |
| PCT/US85/01466 | 8/1985 | WIPO . |

*Primary Examiner*—Corrine McDermott
*Assistant Examiner*—Cris L. Rodriguez
*Attorney, Agent, or Firm*—Blakely, Sokoloff, Taylor & Zafman

[57] ABSTRACT

The invention relates to a catheter and a method of placing a catheter that includes a substantially tubular body portion having an outside diameter no less than the inside diameter of an opening in a catheter introducer adapted to insert a portion of the catheter into a patient's body. The catheter also includes a transition member portion adjacent to a first end of the tubular body portion. The transition member portion has an outside diameter that is less than the outside diameter of the tubular body portion and less than the inside diameter of the opening in the catheter introducer. The invention contemplates that the transition member can be coupled to the end of the tubular body portion, integrally formed with the body portion, or extends from the end of body portion and be removable from a distal end of the body portion. A benefit of the catheter including a transition member portion having an outside diameter that is less than the inside diameter of the opening in the catheter introducer is that it allows a means for inserting a through the introducer catheter which is larger than the inside diameter of the introducer. This provides the benefit of over-the-needle insertion with regard to needle size, but allows for a larger catheter to be placed in the vein by the subsequent removal of the introducer once the transition member portion is placed in the vein.

26 Claims, 5 Drawing Sheets

STEP-DOWN CATHETER

BACKGROUND OF THE INVENTION

1. Field of the Invention

The invention is generally directed to medical catheters and more specifically to the placement of catheters into a patient.

2. Description of Related Art

Catheters are commonplace in the medical field, finding importance in a variety of uses. The term "catheter" is commonly used to identify a tubular instrument that is inserted into a body cavity or orifice, naturally or surgically opened. Vascular catheters, for example, come in many different forms and have many different uses. A vascular catheter typically consists of a hub and tubing or cannula through which fluid flows. The hub may include a flash chamber that allows the individual placing the catheter to see blood in the flash chamber that indicates the catheter has entered a vein. There are different types of vascular catheters. The primary types include the short peripheral, which is typically placed only a short distance (e.g., 2–3 inches) in a vein in the hand or arm of the patient. There are also venous catheters that are longer and include a midline catheter that is placed approximately 6–8 inches in the vein of a patient, and a peripherally inserted central catheter ("PICC") which is placed peripherally, e.g., in the arm of a patient, and fed a significant distance, e.g., to the superior vena cava. Still another type of vascular catheter is the central venous catheter which is typically placed in the internal jugular or subclavien vein, implanted under the skin, tunneled underneath the skin, etc.

One common method of placing a vascular catheter in a patient is through an introducer. In this case, an introducer including a needle, is placed in a patient and into a vein. The needle is then removed, and the catheter is inserted through the introducer into the vein.

A second method of placing a catheter in a patient, often referred to as an Over-The-Needle ("OTN") insertion places the catheter cannula directly over the needle used to introduce the catheter into the vein. The needle is typically connected to a wire or stylet that allows the needle to be removed from the distal or hub end of the catheter cannula once the proximate end of the catheter cannula is placed in the vein. With the needle removed, the catheter is advanced in the vein and placed where desired. The OTN catheter permits the use of a smaller outside diameter needle for a given size outside diameter catheter cannula. The clinical benefit of the OTN approach is the maximization of the size of the catheter placed compared to the size of the needle used. A smaller needle means one can more easily access veins and impart less pain to the patient.

Figure 1:
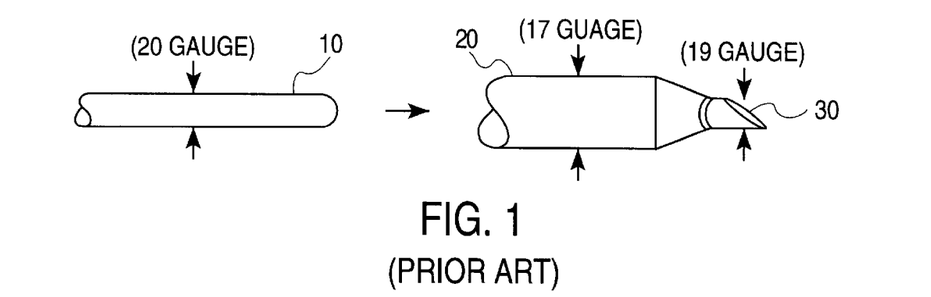
FIG. 1 is a planar side view of a through the introducer catheter introduction configuration.
Figure 2:
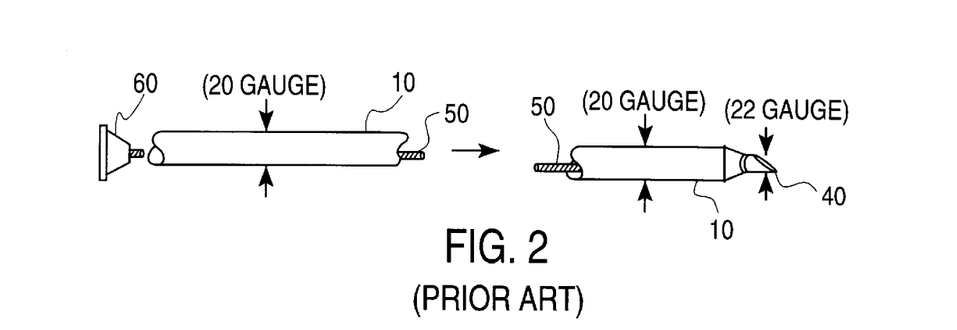
FIG. 2 is a planar side view of an OTN catheter introduction configuration.

FIGS. 1 and 2 illustrate the different types of vascular catheter introduction methods. FIG. 1 illustrates a Through-The-Introducer ("TTI") insertion method and FIG. 2 illustrates an OTN insertion method. In the TTI type insertion, an introducer sheath 20 and needle 30 are inserted into the vein of a patient. Once inserted, the needle 30 is removed, and the catheter cannula 10 is advanced through the introducer sheath 20. When the catheter cannula is placed through the introducer, the maximum outside diameter of the catheter cannula that is placed is slightly smaller than the inside diameter of the introducer, or, slightly smaller than the outside diameter of the needle. In FIG. 1, for example, at least a 19 gauge needle 30 is needed to place a 20 gauge catheter cannula 10.

In the OTN introduction method, a needle 40 is inserted into a patient, the needle 40 being inside a catheter cannula 10 and having a wire or stylet 50 coupled to a hub 60 at the distal end of the catheter cannula 10. Once the needle 40 and a portion of the catheter cannula 10 are inserted into the patient, the needle 40 is removed from the patient by pulling the hub 60 away from the patient. Once the needle 40 is removed, the catheter cannula 10 is advanced to the desired placement in the patient. FIG. 2 illustrates that a smaller outside diameter needle, e.g., 22 gauge, may be used to place a larger outside diameter catheter cannula, e.g., 20 gauge.

SUMMARY OF THE INVENTION

A catheter, catheter kit, and a method of placing a catheter is disclosed. The catheter includes a substantially tubular body portion having an outside diameter no less than the inside diameter of an opening in a catheter introducer adapted to insert a portion of the catheter into a patient's body. The catheter also includes a transition member portion adjacent to a first end of the tubular body portion. The transition member portion has an outside diameter that is less than the outside diameter of the tubular body portion and less than the inside diameter of the opening in the catheter introducer. The invention contemplates that the transition member can be coupled to the end of the tubular body portion, integrally formed with the body portion, or extend through the introductory end of the body portion and be removable from a distal end of the body portion. A benefit of the catheter including a transition member portion having an outside diameter that is less than the inside diameter of the opening in the catheter introducer is that it allows a method for placing a TTI catheter which is larger than the inside diameter of the introducer, by first placing the transition member portion through the introducer. This provides the benefit of OTN insertion with regard to needle size, but allows for a larger catheter to be placed in the vein by the subsequent removal of the introducer once the transition member portion is placed in the vein.

Additional features and benefits of the invention will become apparent from the detailed description, figures, and claims as set forth below.

DETAILED DESCRIPTION OF THE INVENTION

The invention relates to a catheter, a catheter kit, and a method of placing a catheter that includes a substantially tubular body portion and a transition member portion. The substantially tubular body portion has an outside diameter no less than the inside diameter of an opening in a catheter introducer adapted to insert a portion of the catheter into a patient's body. The transition member portion is positioned adjacent to a first end of the tubular body portion. The transition member portion has an outside diameter that is less than the outside diameter of the tubular body portion and less than the inside diameter of the opening in the catheter introducer. The method includes placing an introducer into a patient, providing a catheter with a substantially tubular body portion and a transition member portion, inserting the transition member portion through the opening in the body of the introducer, removing the introducer from the patient, and placing a portion of the tubular body portion of the catheter into the patient. In the following detailed description, specific embodiments of the invention are described with reference to particular materials. Numerous specific details are set forth such as specific materials, configurations, and methods of placing a catheter. It will be obvious, however, to one skilled in the art, that these specific details need not be employed to practice the invention. In other instances, well known materials or methods have not been described in detail in order to avoid unnecessarily obscuring the invention.

Figure 3:
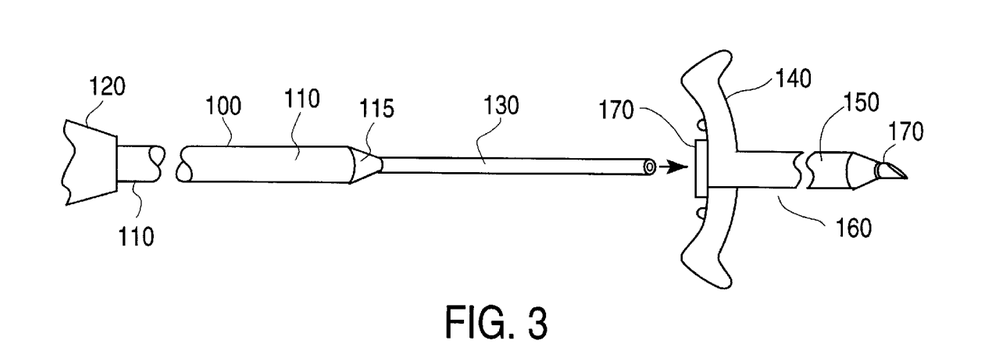
FIG. 3 is a planar side view of the catheter of the invention with a TTI configuration.

FIG. 3 illustrates a planar side view of the catheter configuration of the invention. FIG. 3 shows a catheter 100 made up of a substantially tubular body portion 110 and a transition member portion 130. The substantially tubular body portion or cannula 110 is coupled to a hub 120 at the distal end of the catheter cannula 100. The catheter 100 is configured to be placed in a patient through an introducer 160. The introducer is comprised of handles 140 and a sheath 150. The introducer 160 further includes a removable needle 170. To place the catheter 100 in a patient, the introducer 160 and needle 170 are first placed in the desired location, e.g., the vein, of a patient in a conventional manner. Next, the needle 170 is removed from the distal end of the introducer 160, leaving only the introducer sheath 150 in the patient. Next, the catheter of the invention is inserted through the introducer sheath 150 into the vein. As noted, the catheter 100 includes a transition member portion 130, that has an outside diameter that is less than the inside diameter of the opening in the introducer sheath 150. The transition member portion 130 of the catheter 100 is fed into the vein through the introducer 160. Once the transition member portion 130 is securely placed through the introducer 160 and into the vein, the introducer 160 is removed from the patient and peeled apart or divided and separated from the location near the patient as is common in the prior art. It should be evident that the division of the introducer 160 can be accomplished while the introducer 160 is being removed, for example, to accommodate a shorter transition member portion 130. The tubular body portion 110 of the catheter may then be advanced into the patient by following transition member 130 through the opening made by the needle 170 and the introducer sheath 150. To aid insertion of the tubular body portion 110, the tubular body portion 110 optionally includes a tapered leading edge 115 that gradually opens the existing cut made by the needle 170 in the patient's skin.

The cut made by needle 170 in a patient is large enough to insert the introducer sheath 150, therefore the invention contemplates that the cut will be large enough to accommodate the tubular body portion 110 of the invention. The tubular body portion 110 of the invention has an outside diameter that is no less than the inside diameter of the opening in the catheter introducer 160 or no less than the outside diameter of the needle 170. In one embodiment, the outside diameter or gauge of the tubular body portion 110 of the catheter cannula 100 is approximately the same as the outside diameter of the introducer sheath 150 or the needle 170. In another embodiment, the invention takes advantage of the elastic nature of the skin. The elasticity of the skin allows an opening in the skin, i.e., a needle cut, to stretch approximately 2 gauge sizes to accept an object of a larger diameter than the opening. The invention contemplates, for example, that a cut made by a 22 gauge needle to insert a catheter can accept a 20 gauge catheter using the technique described by the invention.

Figure 4:
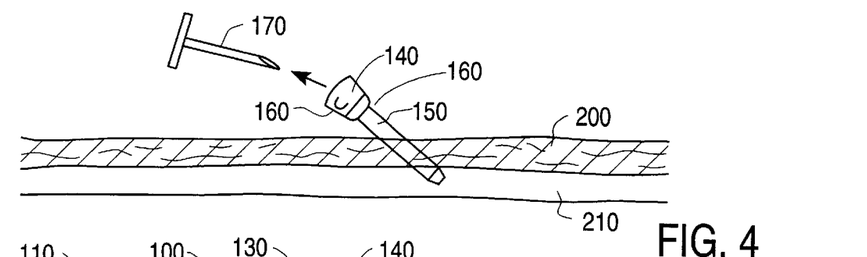
FIGS. 4–9 illustrate the method of the invention of placing a catheter into a patient wherein the transition member portion of the catheter is integral or coupled to the end of the tubular body portion of the catheter.
Figure 5:
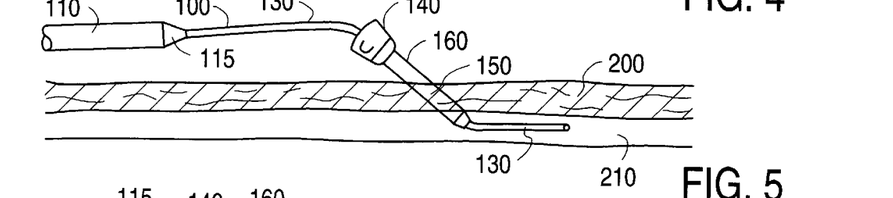
Figures 6, 7:
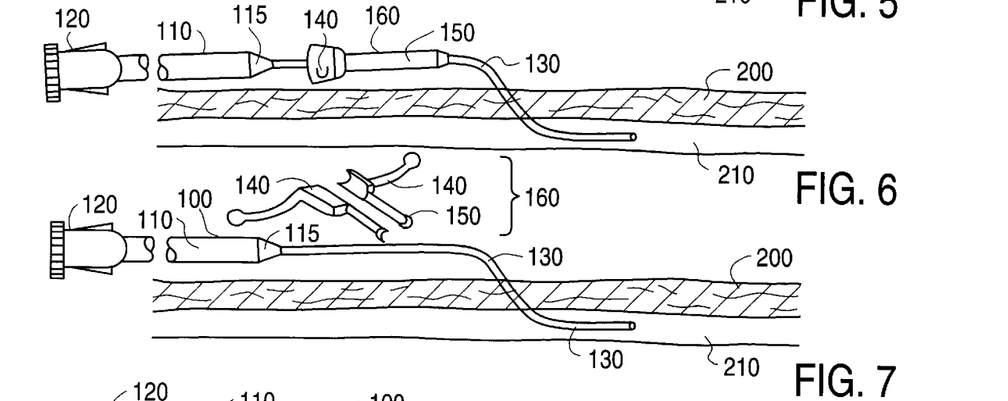

FIGS. 4–9 illustrate a method of inserting the catheter of the invention wherein the transition member portion 130 of the catheter is integral to or coupled to the end of the tubular body portion 110 of the catheter 100. First, as shown in FIG. 4, a needle 170 and introducer 160 including an introducer sheath 150 are placed through the skin 200 of a patient and into a vein 210. Once properly located in the vein 210, the needle 170 is removed from the introducer 160 through the introducer body 140. Next, as shown in FIG. 5, the catheter 100 is placed in the vein 210. The catheter 100 of the invention includes a transition member portion 130 with an outside diameter that is less than the outside diameter of the tubular body portion 110 of the catheter and less than the inside diameter of the introducer sheath 150. For example, the invention contemplates that for a 22 gauge introducer sheath, the invention contemplates that the transition member portion 130 of the catheter 100 has an outside diameter smaller than the inside diameter of the sheath 150. Once placement of the transition member portion 130 of the catheter 100 in the vein 210 is secure, the introducer 160, including the introducer sheath 150, is removed from the vein 210 and the skin 200 of the patient as shown in FIG. 6.

Once the introducer 160 is removed from the skin, FIG. 7 illustrates that the introducer is peeled away from the catheter 100. It is to be noted that the introducer 160 may be peeled away from the catheter 100 while the introducer 160 is being removed, for example, to accommodate a catheter 100 with a shorter transition member portion 130. To facilitate the peeling away and removal of the introducer 160, the introducer handles 140 and sheath 150 may be made of a durable material of varying thickness and a pair of opposed wall portions thinner than the remainder of the introducer 160. In this manner, the introducer 160 is divided at the opposing thinner side walls as shown in FIG. 7.

Alternatively, the introducer handles 140 and sheath 150 may be scored or sliced along opposing sides and divided along the scored or sliced section. Similarly, the sheath 150 is made of a sufficiently thin material so that the sheath 150 may be easily separated when the introducer 160 is divided.

Figure 8:
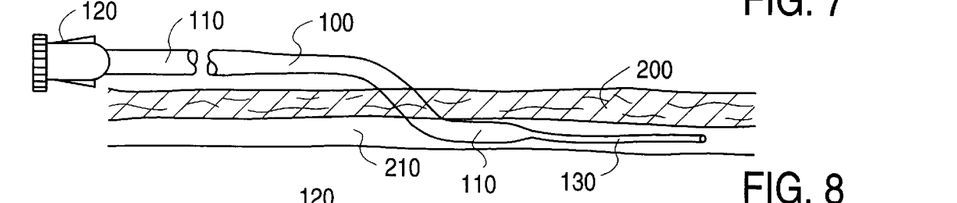

Once the introducer 160 is removed from the target site and no longer encompasses the transition member 130 of the catheter 100, the catheter 100 is further advanced so that the tubular body portion 110 can be inserted into the skin 200 and the vein 210 of the patient. FIG. 8 illustrates the introduction of the tubular body portion 110 into the skin 200 and vein 210 of the patient. The tubular body portion 110 has an outside diameter no less than the inside diameter of the opening in the introducer 160. Taking advantage of the elastic property of the skin 200, the invention contemplates that the tubular portion 110 may be sized approximately 2 gauge sizes larger than the cut made by the needle 170 (and introducer sheath 150). Thus, for a 22 gauge needle 170 opening in the skin 200, the invention contemplates that the tubular body portion 110 of the catheter 100, in one embodiment, have an outside diameter equivalent to a 20 gauge size. The tubular body portion 110 is advanced into the vein to its proper location.

At this point, the invention contemplates different types of transition member portions 130 coupled to the tubular body portion 110 of the catheter 100. In its simplest form, the transition member portion 130 is simply a reduced cross-sectional area/diameter section of the cannula 100 either integrated or coupled to the tubular body portion 110 and made of conventional cannula material including, but not limited to, polypropylene, polyethylene, polyvinyl chloride, polyurethane (PU), TEFLON® (produced by E.I. DuPont de Nemours and Company, Wilmington, Del.), C-FLEX® (produced by Concept, Incorporated, Largo, Fla.), or silicone. Once the catheter 100 is placed, the transition member portion 130 remains a section of reduced diameter lumen at the end of the catheter cannula body. It is to be noted, however, that properties of fluid flow dictate that the fluid flow through the catheter with the reduced lumen portion 130 is better than the fluid flow through a catheter cannula in which the entire lumen has the same dimension as the transition member portion 130. Thus, more fluid can be delivered to the patient through this transitioned catheter than with a catheter with an entire lumen of the dimension of the transition member.

Figure 9:
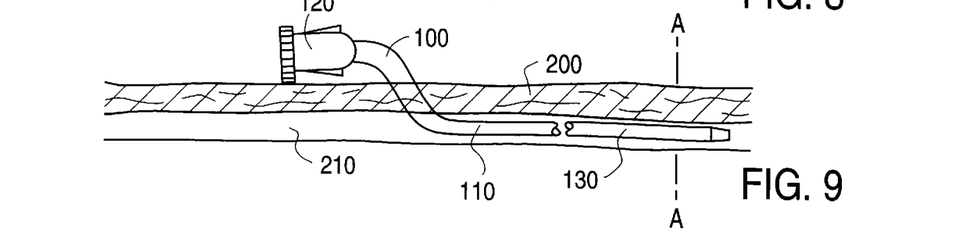

FIG. 9 illustrates an embodiment of the invention wherein after the transition member portion 130 of the catheter 100 is inserted in the patient's body fluid, e.g., blood, the transition member portion 130 assumes a lumen with a cross-sectional area substantially equivalent to the cross-sectional area of the lumen tubular body portion 110. In this case, since the entire cannula 100 will have a cross-sectional area equivalent to the lumen of the tubular body portion 110, the fluid flow through the catheter is improved. In other words, the invention contemplates no reduction in flow capacity through the entire length of the catheter cannula.

Figure 10:
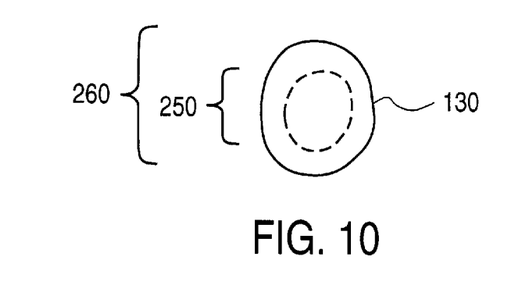
FIG. 10 illustrates a planar cross-sectional view of the transition member portion of the catheter of the invention taken through line A—A of FIG. 9 wherein the transition member portion expands to substantially match the cross-sectional area of the tubular body portion of the catheter.
Figure 11:
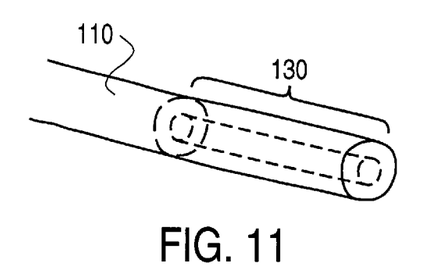
FIG. 11 illustrates a perspective side view of the catheter of the invention including a transition member portion wherein the transition member portion expands to substantially match the diameter of the tubular body portion of the catheter.

FIGS. 10–11 illustrate the embodiment wherein the transition member portion 130 expands to substantially match the cross-sectional area of the tubular body portion 110. The transition member portion 130 is made of a material that swells or expands upon exposure to body fluid. Such a material is Aquavene®, a registered trademark of Menlo Care Corporation of Palo Alto, Calif. Aquavene® is a composite of a hydrogel and an elastomer. This material is described in U.S. Pat. Nos. 4,883,699 and 4,911,691, assigned to Menlo Care. Other materials include thermally-activated hydrogel, hydrogel derivatives, hydrophilic polyurethane, and certain memory polymers.

FIG. 10 shows a transition member portion 130 having a lumen of cross-sectional area of diameter 250 that expands to a cross-sectional area with diameter 260 upon exposure to body fluid. The range of expansion of the catheter area is typically at least two gauge sizes. FIG. 11 illustrates a perspective side view of the catheter cannula having a lumen of the transition member portion 130 that has expanded to substantially match the cross-sectional area of the tubular body portion 110.

Figure 12:
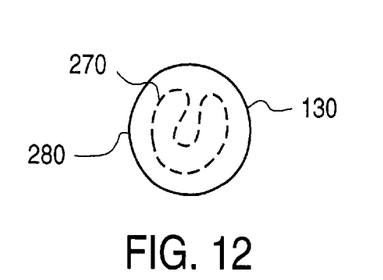
FIG. 12 illustrates a planar cross-sectional view of the transition member portion of the catheter of the invention taken through line A—A of FIG. 9 wherein the transition member portion unfolds to substantially match the cross-sectional area of the tubular body portion of the catheter.
Figures 13, 14:
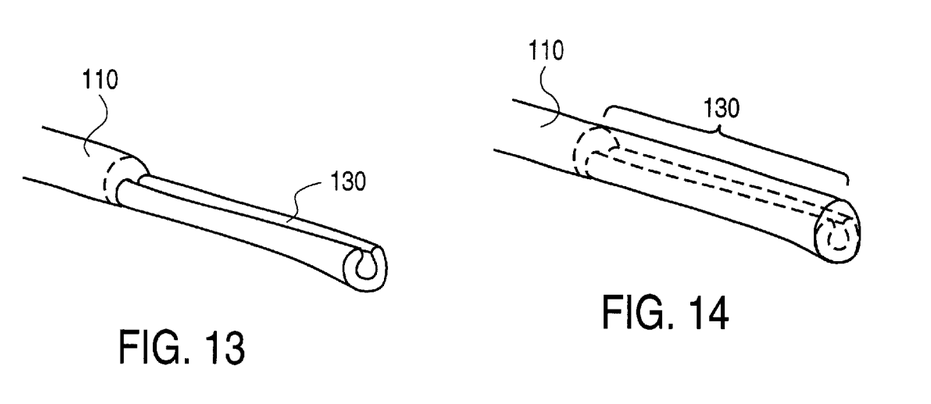
FIG. 13 is a perspective side view of the catheter of the invention wherein the transition member portion is folded to reduce the cross-sectional area of that portion of the catheter.
FIG. 14 illustrates a perspective side view of the catheter of the invention wherein the transition member portion is in an unfolded state to substantially match the cross-sectional area of the tubular body portion of the catheter.

Another embodiment of the catheter with a transition member portion that expands, as shown in FIG. 9, to a lumen with a cross-sectional area that substantially matches the cross-sectional area of the lumen of the tubular body portion is shown in FIGS. 12–14. FIGS. 12–14 illustrate an embodiment wherein the transition member 130 includes a folded state 270 and an unfolded state 280. In the folded state 270, the transition member portion 130 has an area of reduced diameter. In the unfolded state 280, the transition member portion 130 has an outside diameter substantially equivalent to the tubular body portion 110. The folded state 270 is accomplished by longitudinally folding a portion of the transition member 130 inward to reduce the effective outside diameter of the cannula. FIG. 13 illustrates a perspective side view of the transition member in the folded state. FIG. 14 illustrates a perspective side view of the transition member 130 in the unfolded state with an outside diameter substantially equivalent to the outside diameter of the tubular body portion 110.

Figures 15, 16, 17:
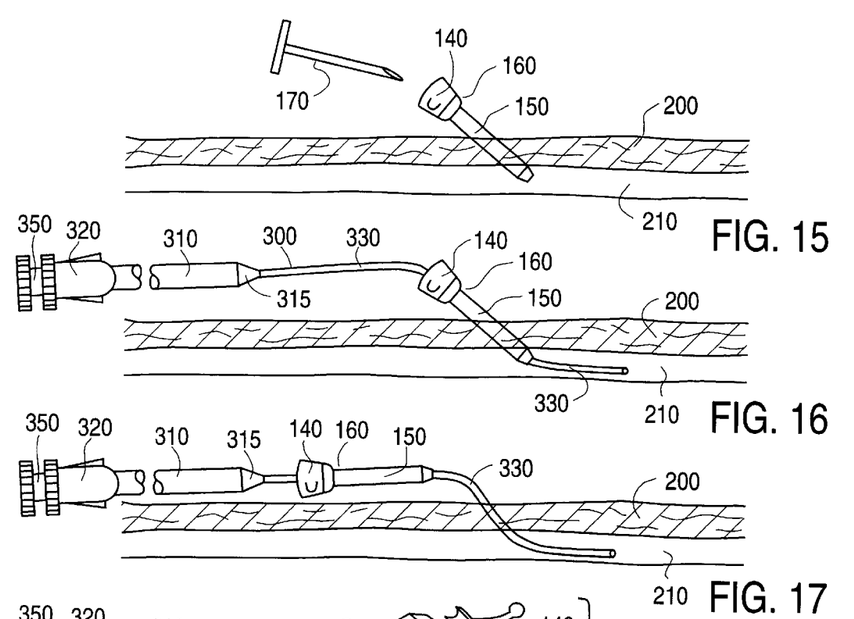
FIGS. 15–20 illustrate a method of inserting the catheter of the invention into a vein of a patient wherein the catheter includes a transition member portion that is separate from the tubular body portion of the catheter and can be removed after or during placement of the tubular body portion.

FIGS. 15–20 illustrates a placement method of a catheter embodiment of the invention wherein the transition portion extends through the lumen of the tubular body portion of the catheter. FIG. 15 illustrates the insertion of an introducer 160 into the vein 210 of a patient. The introducer is placed with a needle 170 so that the introducer sheath 150 and the needle 170 cut the patient's skin and enter the vein 210. Once the needle 170 and introducer sheath 150 are in the patient's vein 210, the needle 170 is removed and the introducer 160 remains.

Next, as illustrated in FIG. 16, the catheter 300 of the invention is inserted through the introducer body 140 and sheath 150 and into the patient's vein 210. In this case, the catheter 300 includes a transition member portion 330 that has an outside diameter that is less than the outside diameter of the tubular body portion 310 and less than the inside diameter of the opening in the catheter introducer 140 and catheter sheath 150. In this embodiment, the transition member portion 330 is not coupled to or integral with the tubular body portion 310, but is connected to a transition member hub 350 and extends through the lumen of the body portion 310. The transition member 330 further extends a significant distance from an end of the tubular body portion 310 to allow the transition member portion 330 to be properly placed in the vein 210 of a patient. Once the transition member portion 330 is properly placed in the patient's vein 210, the introducer 160 is removed from its location in the patient as shown in FIG. 17. Next, the introducer 160 is divided and removed from the area as illustrated in FIG. 18.

Figures 18, 19, 20:
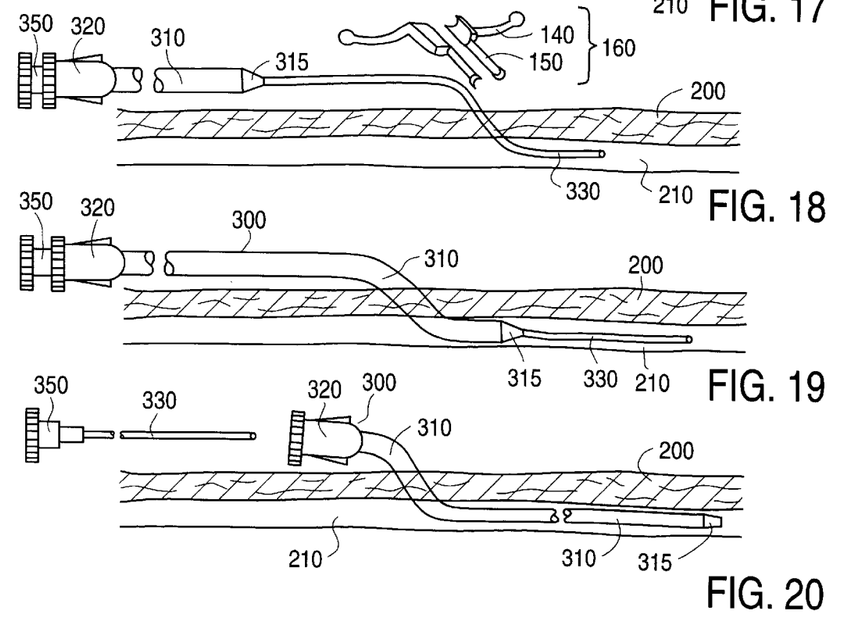

FIG. 19 shows the introduction of the tubular body portion 310 into the patient's vein 210. The tubular body portion 310 includes a tapered section 315 at its end to facilitate insertion into the skin 200 and vein 210. As in the example described with reference to FIGS. 4–9, the invention contemplates that the skin 200 can accommodate approximately a two gauge size larger catheter cannula than the initial needle opening.

Once the tubular body portion 310 is securely placed in the patient's vein 210, the transition member portion 330 is removed from the vein by retracting the transition member portion 330 from a distal end at the catheter hub 320 with the transition member hub 350 as shown in FIG. 20. At this point, the tubular body portion 310 may be further advanced if needed for proper placement.

The above-described embodiment allows a catheter cannula of a single cross-sectional area with an outside diameter larger than the needle (or introducer sheath) opening to be introduced in a patient's vein. This embodiment ensures the full flow benefits of a larger diameter cannula discussed above.

Figure 21:
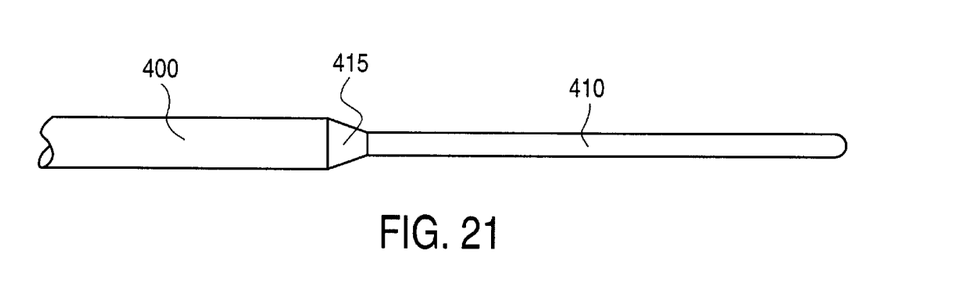
FIG. 21 is a planar side view of an embodiment of the catheter of the invention wherein the transition member portion is comprised of a solid material.

FIGS. 21–24 illustrate various embodiments of catheter assemblies of the invention. FIG. 21 illustrates an embodiment with a tubular body portion 400 and a transition member portion 410 that is a solid material that may be coupled to the tubular body portion 400 or may be separate from the tubular body portion 400 and be removable from the catheter hub. The tubular body portion 400 has a tapered diameter end 415 adjacent the transition member portion 410. The transition member portion 410 has a rounded tip to facilitate insertion. Contemplated materials for this solid transition member portion 410 include any standard flexible, non-toxic material used for catheter production, including, but not limited to, polyurethane, TEFLON®, polypropylene, polyethylene, polyvinyl chloride, or silicone. The surface of the transition portion 410 may further be coated with a low-friction material such as, for example, a hydrogel or TEFLON® to aid insertion.

Copending U.S. Patent Application titled "Thermally Softening Stylet", by Robert Bley, filed Dec. 23, 1996, and given Attorney's Docket No. 56301.P006, describes a thermally softening polymer stylet or guidewire that has sufficient stiffness or column strength to advance through an introducer and suport the guidance of the catheter, but softens as it is exposed to body temperature to provide more patient comfort. The catheter of the invention contemplates that the transition member portion 410, particularly in the embodiment wherein the transition member portion extends through the lumen of the tubular body portion, may be made of a similar material to impart the same properties to the catheter.

Figure 22:
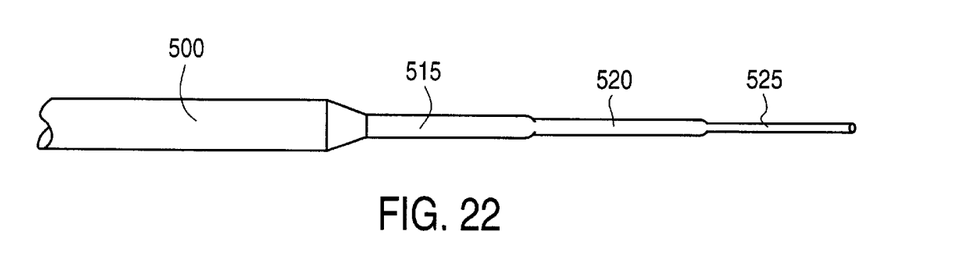
FIG. 22 is a planar side view of the catheter of the invention wherein the transition member portion is transitioned in steps of decreasing diameter or cross-sectional area.

FIG. 22 illustrates an embodiment wherein the transition member portion is transitioned in steps for increased flexibility at the tip of the catheter. In FIG. 22, the transition member portion includes the transition member portions of decreasing cross-sectional area 515, 520, and 525, extending from an end of the tubular body portion 500. Once again, the invention contemplates that the stepped transition portions 515, 520, and 525 may be integrated with or coupled to the end of tubular body portion 500 or may be separate from tubular body portion 500 and extend through the lumen of the tubular body portion 500 and be removed through the catheter hub. Further, it is contemplated that transition member portions 515, 520, and 525 can be a solid piece as described with reference to FIG. 21 or be axially-aligned hollow tubes. In the embodiment wherein transition member portions 515, 520, and 525 are hollow tubes, the invention further contemplates that the transition member portions can remain smaller than the tubular body portion 500 or be made of a material which swells upon exposure to body fluid. Finally, it is to be understood that a varying number of transition steps may make up the stepped-transition portion. FIG. 22 illustrates three portions of varying cross-sectional area for illustrative purposes, but more or less portions may also be employed.

Figure 23:
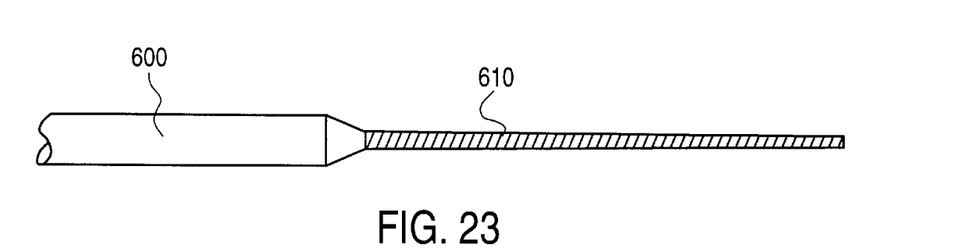
FIG. 23 is a planar side view of an embodiment of the catheter of the invention wherein the transition member portion is a metal or synthetic wire.

FIG. 23 illustrates a catheter having a transition member portion 610 that is a guidewire or stylet. The catheter illustrated in FIG. 23 is separate from the tubular body portion 600 and extends through the tubular body portion 600 and may be removed from the hub of the catheter. The catheter illustrated in FIG. 23 is preferably used in the method described above with reference to FIGS. 15–20 and the accompanying text. Further, the end of the transition member portion may be tapered to impart increased flexibility to the transition member portion 610. Finally, the invention contemplates that the transition member portion 610 may be made of various non-toxic wire material and have a cross-section of varying shape.

Figure 24:
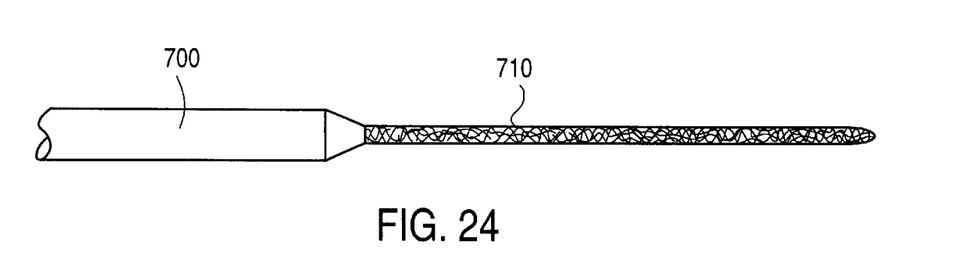
FIG. 24 is a planar side view of an embodiment of the catheter of the invention wherein the transition member portion is a braided or twisted wire.

FIG. 24 illustrates a further embodiment of the catheter of the invention, wherein the transition member portion 710, extending from the tubular body portion 700 is in the form of a guidewire that is a helically-wound wire wrapped around a core and soldered on each end to the core. The helically-wound wire/core transition member portion 710 allows the transition member portion 710 to easily flex and bend which facilitates the placement of the catheter in a patient. Finally, the helically-wound wire/core may be coated with a polymer material that minimizes friction of the catheter in a patient's body. Examples of coatings include, but are not limited to, silicone lubricant, hydrogel, and TEFLON®.

In the preceding detailed description, the invention has been described particularly with reference to vascular catheters. It is to be appreciated, however, that the invention is compatible with other types of catheters that are introduced into the body. Thus, the catheter of the invention and the method of placement of the catheter are intended to be applicable to replace any of the various types of catheter uses, including, but not limited to, vascular, neurological, and urinary drainage catheter uses.

In the preceding detailed description, the invention is described with reference to specific exemplary embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A catheter for use in a catheter assembly including a catheter introducer having an opening and adapted to insert a portion of a catheter into the vascular system of a patient's body through the opening, the catheter comprising:

a substantially tubular body a portion of which is adapted to be placed into a portion of the vascular system of a patient's body, said tubular body having an outside diameter no less than the inside diameter of the opening in a catheter introducer, and an opening of generally uniform inside diameter extending through said tubular body; and a transition member coupled to a first end of said tubular body, said transition member having an opening of generally uniform diameter extending through said transition member and axially aligned with the opening in said tubular body and a first configuration including an outside diameter that is less than the outside diameter of said tubular body and less than said inside diameter of the opening in said the catheter introducer and a second configuration including a diameter of the opening substantially equivalent to the diameter of the opening of said tubular body.

2. The catheter of claim 1, wherein said tubular body of said catheter has an opening of generally uniform diameter extending through said tubular body, and wherein said transition member comprises a substantially tubular body with an opening extending through said transition member and axially aligned with said tubular body, said transition member further comprising a proximate portion and a distal portion, wherein said outside diameter of said proximate portion is larger than said outside diameter of said distal portion.

3. A catheter assembly comprising:

a catheter introducer having an opening and adapted to insert a portion of a catheter into the vascular system of a patient's body through the opening:

a catheter comprising:

a substantially tubular body a portion of which is adapted to be placed into a portion of the vascular system of a patient's body, said tubular body having an outside diameter no less than the inside diameter of the opening in said catheter introducer, and an opening of generally uniform inside diameter extending through said tubular body;

a transition member integrally formed with a first end of said tubular body, said transition member having an opening of generally uniform diameter extending through said transition member and axially aligned with the opening in said tubular body and a first configuration including an outside diameter that is less than the outside diameter of said tubular body and less than said inside diameter of the opening in said catheter introducer and a second configuration including a diameter of the opening substantially equivalent to the diameter of the opening of said tubular body.

4. The catheter assembly of claim 3, wherein said transition member of said catheter is a composite of a hydrogel and an elastomer.

5. The catheter assembly of claim 3, wherein said transition member of said catheter has a substantially tubular body with an opening extending through said transition member and a wall wherein said transition member includes a folded state wherein a portion of said wall is longitudinally folded inward.

6. The catheter assembly of claim 5, wherein said transition member of said catheter includes an unfolded state wherein in said unfolded state said outside diameter of said transition member is substantially equivalent to said outside diameter of said tubular body.

7. The catheter assembly of claim 3, wherein said catheter introducer is comprised of a body of a durable material and an opening extending through said body, wherein said body includes a first portion having a first thickness and a pair of opposed second portions having a second thickness that is less than said first thickness and wherein said opposed second portions substantially extend said length of said body, and wherein said body is adapted to be divided along said second portions.

8. The catheter assembly of claim 3, wherein said tubular body of said catheter has an opening of generally uniform diameter extending through said tubular body, and wherein said transition member comprises a substantially tubular body with an opening extending through said transition member and axially aligned with said tubular body, said transition member further comprising a proximate portion and a distal portion, wherein said outside diameter of said proximate portion is larger than said outside diameter of said distal portion.

9. A catheter assembly comprising:

a catheter introducer having an opening adapted to insert a portion of a catheter into the vascular system of a patient's body through said opening;

a catheter comprising:

a substantially tubular body a portion of which is adapted to be placed into a portion of the vascular system of a patient, said tubular body having a first end and a second end distal to said first end and an outside diameter no less than an inside diameter of the opening in said catheter introducer, and a transition member having an outside diameter that is less than said outside diameter of said tubular body and less than said inside diameter of said opening in said catheter introducer, and a length that is greater than a length of said tubular body, wherein said transition member is a guide wire that in one configuration is axially aligned with said tubular body and extends from each of said first end and said second end of said tubular body.

10. The catheter assembly of claim 9, wherein said transition member of the catheter is adapted to be removed from said second end of said tubular body of the catheter.

11. A method of placing a vascular catheter in a patient through an introducer, said method comprising:

placing an introducer into a patient, said introducer having a body and an opening extending through said body;

providing a vascular catheter with a substantially tubular body portion having a first end and an outside diameter no less than the inside diameter of said opening in said introducer and a transition member portion integrally formed with said first end of said tubular body portion, said transition member portion having a first end and said transition member having an outside diameter that is less than said inside diameter of said opening in said introducer;

inserting said first end of said transition member portion through said opening in said body of said introducer and into a portion of the vascular system of the patient;

removing said introducer from the patient;

separating said introducer from said catheter; and placing a portion of said tubular body portion of said catheter into the portion of the vascular system of the patient.

12. The method of claim 11, wherein said tubular body portion of said catheter has an opening of generally uniform diameter extending through said tubular body portion, and wherein said transition member portion has an opening of a generally uniform first diameter extending through said transition member portion and axially aligned with said tubular body portion.

13. The method of claim 12, wherein said transition member portion is comprised of an expandable material adapted to expand said opening of said transition member portion to a second diameter such that said second diameter is larger than said first diameter.

14. The method of claim 13, wherein said transition member portion is a composite of a hydrogel and an elastomer.

15. The method of claim 11, wherein said transition member portion of said catheter has a substantially tubular body with an opening extending through said transition member portion and a wall wherein said transition member portion includes a folded state wherein a portion of said wall is longitudinally folded inward.

16. The method of claim 15, wherein said transition member portion includes an unfolded state wherein in said unfolded state said outside diameter of said transition member portion is substantially equivalent to said outside diameter of said tubular body portion.

17. The method of claim 11, wherein said tubular body portion of said catheter has an opening of generally uniform diameter extending through said tubular body portion, and wherein said transition member portion of said catheter comprises a substantially tubular body with an opening extending through said transition member portion and axially aligned with said tubular body portion, said transition member portion further comprising a proximate portion and a distal portion, wherein said outside diameter of said proximate portion is larger than said outside diameter of said distal portion.

18. The method of claim 11, wherein said introducer is comprised of a body of a durable material and an opening extending through said body, wherein said body includes a first portion having a first thickness and a pair of opposed second portions having a second thickness that is less than said first thickness and wherein said opposed second portions substantially extend said length of said body, and wherein after said step of removing said introducer the method further comprises dividing said introducer along said second portions and separating said introducer from said catheter.

19. A method of placing a vascular catheter in a patient through an introducer, said method comprising:

placing an introducer into a portion of the vascular system of a patient, said introducer having a body and an opening extending through said body;

providing a vascular catheter with a substantially tubular body having a first end and a second end distal to said first end, said tubular body having an outside diameter no less than the inside diameter of said opening in said introducer and a transition member adjacent to a first end of said tubular body portion, said transition member portion having an outside diameter that is less than said outside diameter of a tubular body portion and less than said inside diameter of said opening in said introducer, wherein said transition member portion of said catheter is a guide wire and wherein said transition member is axially aligned with said tubular body of said catheter and extends from said first end of said tubular body;

inserting said transition member portion through said opening in said body of said introducer;

removing said introducer from the patient;

separating said introducer from said catheter;

placing a portion of said tubular body portion of said catheter into a vascular portion of the patient; and removing said transition member from a second end of said tubular body.

20. The method of claim 19, wherein said tubular body has an opening of generally uniform diameter extending through said tubular body, and wherein said transition member extends through said opening of said tubular body, said method further comprising the step of removing said transition member from said catheter from a second end of said tubular body.

21. A catheter kit comprising:

a catheter introducer having an opening, said catheter introducer adapted to insert a portion of a catheter into a patient's body; and a catheter including a substantially tubular body having a first end and a second end distal to said first end, said first end adapted to be placed into a patient's body and a transition member adjacent to said first end of said tubular body, wherein said tubular body has an outside diameter no less than the inside diameter of the opening in said introducer, and wherein said transition member has an outside diameter that is less than the inside diameter of the opening in said introducer, wherein said transition member has a substantially tubular body with an opening extending through said transition member and a wall wherein said transition member includes a folded state wherein a portion of said wall is longitudinally folded inward.

22. The kit of claim 21, wherein said transition member includes an unfolded state wherein in said unfolded state said outside diameter of said transition member is substantially equivalent to said outside diameter of said tubular body.

23. A catheter kit comprising:

a catheter introducer having an opening, said catheter introducer adapted to insert a portion of a catheter into a patient's body:

a catheter including a substantially tubular body having a first end and a second end distal to said first end, said first end adapted to be placed into a patient's body and a transition member adjacent to said first end of said tubular body, and wherein said tubular body has an outside diameter no less than the inside diameter of the opening in said introducer, and wherein said transition member has an outside diameter that is less than the inside diameter of the opening in said catheter introducer, wherein said tubular body has an opening of generally uniform diameter extending through said tubular body, and wherein said transition member comprises a substantially tubular body with an opening extending through said transition member and axially aligned with said tubular body, said transition member further comprising a proximate portion and a distal portion, wherein said outside diameter of said proximate portion is larger than said outside diameter of said distal portion.

24. A catheter kit comprising:

a catheter introducer having an opening, said catheter introducer adapted to insert a portion of a catheter into a patient's body, and a catheter including a substantially tubular body having a first end and a second end distal to said first end, said first end adapted to he placed into a patient's body and a transition member adjacent to said first end of said tubular body, wherein said tubular body has an outside diameter no less than the inside diameter of the opening in said introducer, and wherein said transition member has an outside diameter that is less than the inside diameter of the opening in said catheter introducer, wherein said transition member is a guide wire and wherein said transition member is separable from said tubular body and axially aligned with said tubular body and in a first configuration extends from said first end of said tubular body and from said second end of said tubular body.

25. The kit of claim 24, wherein said tubular body has an opening of generally uniform diameter extending through said tubular body, and wherein said transition member extends through said opening of said tubular body.

26. The kit of claim 25, wherein said transition member is adapted to be removed from said second end of said tubular body.

* * * * *